US00RE44894E

(19) United States
(12) Reissued Patent
Hirai

(10) Patent Number: US RE44,894 E
(45) Date of Reissued Patent: May 13, 2014

(54) METHOD OF DETECTING OR QUANTITATIVELY DETERMINING MITOCHONDRIAL DNA 3243 VARIATION, AND KIT THEREFOR

(75) Inventor: Mitsuharu Hirai, Kyoto (JP)

(73) Assignee: ARKRAY, Inc., Kyoto (JP)

(21) Appl. No.: 13/234,907

(22) Filed: Sep. 16, 2011

Related U.S. Patent Documents

Reissue of:
(64) Patent No.: 7,625,723
Issued: Dec. 1, 2009
Appl. No.: 10/553,576
PCT Filed: Apr. 16, 2004
PCT No.: PCT/JP2004/005496
§ 371 (c)(1),
(2), (4) Date: Oct. 17, 2005
PCT Pub. No.: WO2004/092415
PCT Pub. Date: Oct. 28, 2004

(30) Foreign Application Priority Data

Apr. 16, 2003 (JP) ..... 2003-111173
Apr. 18, 2003 (JP) ..... 2003-114382

(51) Int. Cl.
*C12Q 1/68* (2006.01)
*C12P 19/34* (2006.01)

(52) U.S. Cl.
USPC ..... 435/6.11; 435/6.12; 435/91.2

(58) Field of Classification Search
USPC ..... 435/6.11, 6.12, 91.2
See application file for complete search history.

(56) References Cited

U.S. PATENT DOCUMENTS

| | | | | |
|---|---|---|---|---|
| 6,979,541 | B1 * | 12/2005 | Pont-Kingdon et al. | 435/6.14 |
| 7,081,226 | B1 * | 7/2006 | Wittwer et al. | 422/68.1 |
| 2002/0106653 | A1 | 8/2002 | Kurane et al. | |

FOREIGN PATENT DOCUMENTS

| | | |
|---|---|---|
| JP | 11-221077 | 8/1999 |
| JP | 2001-286300 | 10/2001 |
| JP | 2002-119291 | 4/2002 |
| WO | WO 02/057414 | 7/2002 |
| WO | WO 02/072875 * | 9/2002 |

OTHER PUBLICATIONS

Majarnaa et al., Epidemiology of A3243G, the Mutation for Mitochondrial Encephalomyopathy, Lactic Acidosis, and Strokelike Episodes: Prevalence of the Mutation in an Adult Population, Am. J. Hum. Genet. 63-447-454, 1998.*
Howell et al., Dynamic allele-specific hybridization, Nature Biotechnology vol. 17 Jan. 1999. http://biotech.nature.com.*
Froguel et al., Familial Hyperglycemia Due to Mutations in Glucokinase—Definition of a Subtype of Diabetes Mellitus, The New England Journal of Medicine, Mar. 11, 1993, No. 10, vol. 328:697-70.*
Buck et al., Design Strategies and Performance of Custom DNA Sequencing Primers, BioTechniques 27:528-536 (Sep. 1999).*
Mackay et al., Real-time PCR in virology, Nucleic Acids Res. Mar. 15, 2002; 30(6): 1292-1305. Acrobat format.*
Mackay et al., Real-time PCR in virology, Nucleic Acids Res. Mar. 15, 2002; 30(6): 1292-1305. HTML format.*
Loeffler, et al. "Rapid Detection of Point Mutations by Fluorescence Resonance Energy Transfer and Probe Melting Curves in *Candida* Species," *Clinical Chemistry,* vol. 46, No. 5, pp. 631-635, 2000.
Nakamura, et al. Detection of mit DNA Point Mutations by Mutation-Specific PCR, *Nippon Rinsho,* vol. 55, No. 12, pp. 3277-3281, Dec. 1997.
Odawara, et al. "Selection of Primers for Detection of A to G Mutation at Nucleotide 3243 of the Mitochondrial Gene," *Diabetologia,* vol. 38, No. 3, pp. 377-378, 1995.
Seibel, et al. "A Rapid and Sensitive PCR Screenings Method for Point Mutations Associated with Mitochondrial Encephalomyopathies," *Biochemical and Biophysical Research Communications,* vol. 200, No. 2, pp. 938-942, Apr. 29, 1994.
Tsukuda, et al. "Screening of Patients with Maternally Transmitted Diabetes for Mitochondrial Gene Mutations in the $tRNA^{lau(UUR)}$ Region," *Diabetic Medicine,* vol. 14, pp. 1032-1037, 1997.
Zhang et al., "Occurrence of a Particular Base Substitution (3243 A to G) in Mitochondrial DNA of Tissues of Ageing Humans," *Biochemical and Biophysical Research Communications,* vol. 195, No. 2, pp. 1104-1110, Sep. 15, 1993.
International Search Report dated Jul. 2, 2004.
Wei, et al. "Decreased Cellular Respiratory Function and Mitochondrial DNA Mutations in the Human Heart Associated with Ageing and Disease," *Asia Pacific Heart Journal,* vol. 6, No. 3, pp. 197-204, Dec. 1997.
Supplementary Partial European Search Report dated Oct. 30, 2006.
Notice of Reason for Rejection issued on Nov. 25, 2008 in a related Japanese patent application with English Translation.
Siebel, et al., "A Rapid and Sensitive PCR Screening Method for Point Mutations Associated with Mitochondrial Encephalomyopathies," *Biochemical and Biophysical Research Communications,* vol. 200, No. 2, pp. 938-942, Apr. 1994.
Tsukuda, et al. "Screening of Patients with Maternally transmitted Diabetes for Mitochondrial Gene Mutations in the $tRNA^{Leu(UUR)}$ Region," *Diabetic Medicine,* vol. 14, pp. 1032-1037, 1997.
"Selection of Primers for Detection of A to G Mutation at Nucleotide 3243 of the Mitochondrial Gene," *Diabetologia,* vol. 38, No. 3, pp. 377-378, 1995.

* cited by examiner

*Primary Examiner* — Kenneth Horlick
(74) *Attorney, Agent, or Firm* — Morgan, Lewis & Bockius LLP

(57) ABSTRACT

A method for detecting a DNA having the mitochondrial DNA 3243 mutation is disclosed. Quantitative PCR is used with a primer having a nucleotide sequence complementary to the nucleotide sequence starting from the nucleotide number 243 in SEQ ID NO: 2 and having a length of 12 to 30 nucleotides. A method is also disclosed for detecting a DNA having the mitochondrial DNA 3243 mutation by using a nucleic acid probe which is end labeled with a fluorescent dye. The fluorescence of the fluorescent dye decreases upon hybridization. The nucleic acid probe has a nucleotide sequence complementary to the nucleotide sequence starting from nucleotide number 230 in the nucleotide sequence of SEQ ID NO: 2 and a length of 14 to 40 nucleotides. The 3' end of the probe is labeled with the fluorescent dye.

11 Claims, 6 Drawing Sheets

Wild sequence cccaagaacagggtttgttaagatggcagAgcccggtaatcgcataaaac

Mutant sequence cccaagaacagggtttgttaagatggcagGgcccggtaatcgcataaaac gggcCctgccatcttaac ggcCctgccatcttaac

METHOD OF DETECTING OR QUANTITATIVELY DETERMINING MITOCHONDRIAL DNA 3243 VARIATION, AND KIT THEREFOR

Matter enclosed in heavy brackets [ ] appears in the original patent but forms no part of this reissue specification; matter printed in italics indicates the additions made by reissue.

RELATED APPLICATIONS

This is the U.S. National Phase under 35 U.S.C. §371 of International Application PCT/JP2004/005496, filed Apr. 16, 2004, which was published in a language other than English which claims priority of JP 2003-111173, filed Apr. 16, 2003 and JP 2003 114382, filed Apr. 18, 2003.

*Sequence Listing Submission via EFS-Web*

*A computer readable text file, entitled "SequenceListing.txt," created on or about Oct. 17, 2005 with a file size of about 7 kb contains the sequence listing for this application and is hereby incorporated by reference in its entirety.*

TECHNICAL FIELD

The present invention relates to methods for detecting and quantifying mitochondrial DNA 3243 mutation and a kit therefor.

BACKGROUND ART

The A→G mutation at the 3243rd position of mitochondrial DNA (mt3243) is a mutation existing in 1% of Japanese diabetes mellitus patients, and occurs at the highest frequency among diabetic conditions caused by abnormality of a single gene. One of the characteristics of abnormality of mitochondrial genes is coexistence of normal and abnormal mitochondrial DNAs in various proportions, and this state is referred to as heteroplasmy. The ratio of mt3243 mutation heteroplasmy is said to relate to progression degree of the pathological condition, and it is considered that it can be used for the determination of progression degree of the pathological condition or therapeutic effect.

If the mt3243 mutation exists, a recognition site of a restriction enzyme emerges at the position of the mutation. Therefore, the mutation can be detected by a method of amplifying DNA by PCR so that a portion including the mutation position should be amplified, digesting the amplification product with a restriction enzyme and determining whether the DNA has been digested or not by electrophoresis (PCR-RFLP) (for example, refer to The Japanese Journal of Clinical Pathology, vol. 44, 8, pp. 778-782, 1996).

Because PCR amplifies templates of several molecules several billion times, even a trace amount of contaminant may cause a false positive or false negative result. In PCR-RFLP, the amplification product needs to be collected and subjected to a treatment with a restriction enzyme after PCR, and therefore the amplification product may contaminate the subsequent reaction system. Accordingly, a false positive or false negative result may be obtained.

Further, DNA is treated with a restriction enzyme and then subjected to electrophoresis after completion of PCR. Therefore, time required for the detection becomes extremely long. In addition, because the procedure is complicated, automatization is difficult. Furthermore, because denaturation and annealing are repeated during PCR, a normal type sequence and a mutant type sequence may erroneously bind to each other. Such a product is not recognized by a restriction enzyme, and therefore it is not digested (DNA is digested by a restriction enzyme only when both of the double strands are of mutant type). Accordingly, in the quantification of the ratio of heteroplasmy, the proportion of the mutant type becomes lower than the actual value.

Meanwhile, as an allele specific amplification method, a method called MASA (mutant allele specific amplification) method is known (for example, refer to Sekiya T. et al. ed., "PCR Front Line—From Basic Techniques To Applications", Kyoritsu Shuppan, pp. 140-142, 1997). In this method, the mutation allele is specifically amplified by performing PCR using a primer pair designed so that the 3' end of one primer should be a mutated nucleotide.

Further, a method is also known in which by using a system in which fluorescence changes depending on amount of an amplification product; PCR amplification product is quantified on a real time basis by measuring fluorescence; and on the basis of the results, nucleic acids in a sample are quantified (real time quantitative PCR). By performing the MASA method in accordance with this method, an amplification product obtained by the MASA method can be quantified.

Furthermore, a method is generally known in which a region containing a mutation is amplified by PCR, then a melting curve analysis is performed by using a nucleic acid probe labeled with a fluorescent dye, and the mutation is analyzed on the basis of the result of the melting curve analysis (Clinical Chemistry, vol. 46, 5, pp. 631-635, 2000; Japanese Patent Application Laid-open (Kokai) No. 2002-119291).

DISCLOSURE OF THE INVENTION

An object of the present invention is to provide methods for detecting and quantifying the mt3243 mutation and a kit therefor. Further, another object of the present invention is to identify a quenching probe effective for the detection of the mt3243 mutation and thereby provide a method for detecting the mt3243 mutation and a kit therefor.

The inventors of the present invention found that by designing a primer pair on the basis of a specific region containing the mt3243 mutation in a mitochondrial DNA, the mt3243 mutation could be detected by the MASA method.

The literature concerning the aforementioned method of using a probe only teaches that, concerning the design of the probe, the probe should be designed so that, when a quenching probe having an end labeled with a fluorescent dye hybridizes with a target nucleic acid, two or more nucleotide pairs of the probe-nucleic acid hybrid should form at least one pair of G and C in the end portion. With regard to the mt3243 mutation, the inventors of the present invention designed a quenching probe satisfying the aforementioned condition and attempted the detection. However, no quenching probe that enabled detection was easily obtained.

The inventors of the present invention found that by designing a quenching probe based on a specific region containing the mt3243 mutation, the mt3243 mutation could be detected by a melting curve analysis using the quenching probe.

The present invention was accomplished on the basis of the above findings and provides the followings.

(1) A method for detecting a DNA having the mitochondrial DNA 3243 mutation comprising performing PCR using a DNA obtained from a sample as a template and detecting an amplification product, wherein primers used for PCR include a primer having a nucleotide sequence complementary to a nucleotide sequence starting from the nucleotide number 243 in the nucleotide sequence of SEQ ID NO: 2 and having a length of 12 to 30 nucleotides.

(2) The method according to (1), wherein the primers used for PCR comprise a primer having the nucleotide sequence of SEQ ID NO: 3 and a primer having the nucleotide sequence of SEQ ID NO: 5.

(3) A method for quantifying a DNA having the mitochondrial DNA 3243 mutation comprising performing quantitative PCR using a DNA obtained from a sample as a template and quantifying an amplification product, wherein the quantitative PCR is a method of using a system in which fluorescence changes depending on amount of an amplification product to quantify the amplification product in PCR on real time basis by measurement of fluorescence and quantifying the DNA in the sample on the basis of the result of the measurement, and primers used for the quantitative PCR comprise a primer having a nucleotide sequence complementary to a nucleotide sequence starting from the nucleotide number 243 in the nucleotide sequence of SEQ ID NO: 2 and having a length of 12 to 30 nucleotides.

(4) The method according to (3), wherein the primers used for the quantitative PCR comprises a primer having the nucleotide sequence of SEQ ID NO: 3 and a primer having the nucleotide sequence of SEQ ID NO: 5.

(5) A method for determining a heteroplasmy ratio of the mitochondrial DNA 3243 mutation contained in a sample, which comprises:

(a) quantifying a DNA having the mitochondrial DNA 3243 mutation by the method as defined in (3) or (4), (b) quantifying mitochondrial DNAs by a method for quantifying mitochondrial DNAs comprising performing quantitative PCR using a DNA obtained from a sample as a template and quantifying an amplification product, wherein the quantitative PCR uses a system in which fluorescence changes depending on amount of an amplification product to quantify the amplification product in PCR on real time basis by measurement of fluorescence, and DNAs in the sample is quantified on the basis of the result of the measurement, and (c) calculating the heteroplasmy ratio of the mitochondrial DNA 3243 mutation from the results of (a) and (b).

(6) The method according to (5), wherein the primers used in the step (b) comprises a primer having the nucleotide sequence of SEQ ID NO: 3 and a primer having the nucleotide sequence of SEQ ID NO: 4.

(7) The method according to any one of (3) to (6), wherein the system comprises a nucleic acid probe of which 5' end is labeled with a fluorescent dye, and in which fluorescence of the fluorescent dye decreases upon hybridization, wherein the-nucleic acid probe has a nucleotide sequence starting from the nucleotide number 212 or 215 in the nucleotide sequence of SEQ ID NO: 1 and having a length of 15 to 40 nucleotides or a nucleotide sequence starting from the nucleotide number 222 in the nucleotide sequence of SEQ ID NO: 2 and having a length of 15 to 40 nucleotides, or a nucleic acid probe of which 3' end is labeled with a fluorescent dye, in which fluorescence of the fluorescent dye decreases upon hybridization, and which has a nucleotide sequence complementary to a nucleotide sequence starting from the nucleotide number 230 in the nucleotide sequence of SEQ ID NO: 2 and having a length of 14 to 40 nucleotides, and fluorescence of the fluorescent dye is measured.

(8) A kit for the method as defined in (1), which comprises a primer having a nucleotide sequence complementary to a nucleotide sequence starting from the nucleotide number 243 in the nucleotide sequence of SEQ ID NO: 2 and having a length of 12 to 30 nucleotides.

(9) The kit according to (8), which comprises a primer having the nucleotide sequence of SEQ ID NO: 3 and a primer having the nucleotide sequence of SEQ ID NO: 5.

(10) A kit for the method as defined in (3), which comprises a primer having a nucleotide sequence complementary to a nucleotide sequence starting from the nucleotide number 243 in the nucleotide sequence of SEQ ID NO: 2 and having a length of 12 to 30 nucleotides.

(11) The kit according to (10), which comprises a primer having the nucleotide sequence of SEQ ID NO: 3 and a primer having the nucleotide sequence of SEQ ID NO: 5.

(12) A kit for the method as defined in (5), which comprises a first primer pair comprising a primer having a nucleotide sequence complementary to a nucleotide sequence starting from the nucleotide number 243 in the nucleotide sequence of SEQ ID NO: 2 and having a length of 12 to 30 nucleotides, and a second primer pair for quantifying mitochondrial DNAs.

(13) The kit according to (12), wherein the first primer pair comprises a primer having the nucleotide sequence of SEQ ID NO: 3 and a primer having the nucleotide sequence of SEQ ID NO: 5.

(14) The kit according to (12), wherein the second primer pair comprises a primer having the nucleotide sequence of SEQ ID NO: 3 and a primer having the nucleotide sequence of SEQ ID NO: 4.

(15) The kit according to any one of (10) to (14), which further comprises a nucleic acid probe of which 5' end is labeled with a fluorescent dye, in which fluorescence of the fluorescent dye decreases upon hybridization, and which has a nucleotide sequence starting from the nucleotide number 212 or 215 in the nucleotide sequence of SEQ ID NO: 1 and having a length of 15 to 40 nucleotides or a nucleotide sequence starting from the nucleotide number 222 in the nucleotide sequence of SEQ ID NO: 2 and having a length of 15 to 40 nucleotides, or a nucleic acid probe of which 3' end is labeled with a fluorescent dye, in which fluorescence of the fluorescent dye decreases upon hybridization, and which has a nucleotide sequence complementary to a nucleotide sequence starting from the nucleotide number 230 in the nucleotide sequence of SEQ ID NO: 2 and having a length of 14 to 40 nucleotides.

(16) A nucleic acid probe of which end is labeled with a fluorescent dye, and in which fluorescence of the fluorescent dye decreases upon hybridization, wherein the nucleic acid probe has a nucleotide sequence complementary to a nucleotide sequence starting from the nucleotide number 230 in the nucleotide sequence of SEQ ID NO: 2 and having a length of 14 to 40 nucleotides, and the 3' end of the probe is labeled with the fluorescent dye.

(17) The nucleic acid probe according to (16), wherein the nucleic-acid probe has the nucleotide sequence of SEQ ID NO: 21 or 22.

(18) A method for detecting a mutation comprising performing a melting curve analysis for a nucleic acid having a single nucleotide polymorphism site by using a nucleic acid probe labeled with a fluorescent dye and measuring fluorescence of the fluorescent dye, and detecting the mutation on the basis of the result of the melting curve analysis, wherein the single nucleotide polymorphism is a mutation at the 3243rd position in a mitochondrial DNA, and the nucleic acid probe is the nucleic acid probe as defined in (16) or (17).

(19) The method according to (18), wherein a region containing a single nucleotide polymorphism site in a nucleic acid contained in a sample is amplified to obtain the nucleic acid showing the single nucleotide polymorphism.

(20) The method according to (19), wherein the amplification is performed by a method of using a DNA polymerase.

(21) The method according to (20), wherein the amplification is performed in the presence of a nucleic acid probe.

(22) A kit for the method as defined in (18), which comprises a nucleic acid probe of which end is labeled with a fluorescent dye, and in which fluorescence of the fluorescent dye decreases upon hybridization, wherein the nucleic acid probe has a nucleotide sequence complementary to a nucleotide sequence starting from the nucleotide number 230 in the nucleotide sequence of SEQ ID NO: 2 and having a length of 14 to 40 nucleotides, and the 3' end of the probe is labeled with the fluorescent dye.

(23) The kit according to (22), wherein the nucleic acid probe has the nucleotide sequence of SEQ ID NO: 21 or 22.

(24) The kit according to (22) or (23), which further comprises a primer for amplifying a region containing the 3243rd mutation in a mitochondrial DNA by a method of using a DNA polymerase.

In the present specification, a nucleotide sequence complementary to an objective nucleotide sequence means a nucleotide sequence complementary to the objective nucleotide sequence for the full length of the objective nucleotide sequence.

BEST MODE FOR CARRYING OUT THE INVENTION

Figure 1:
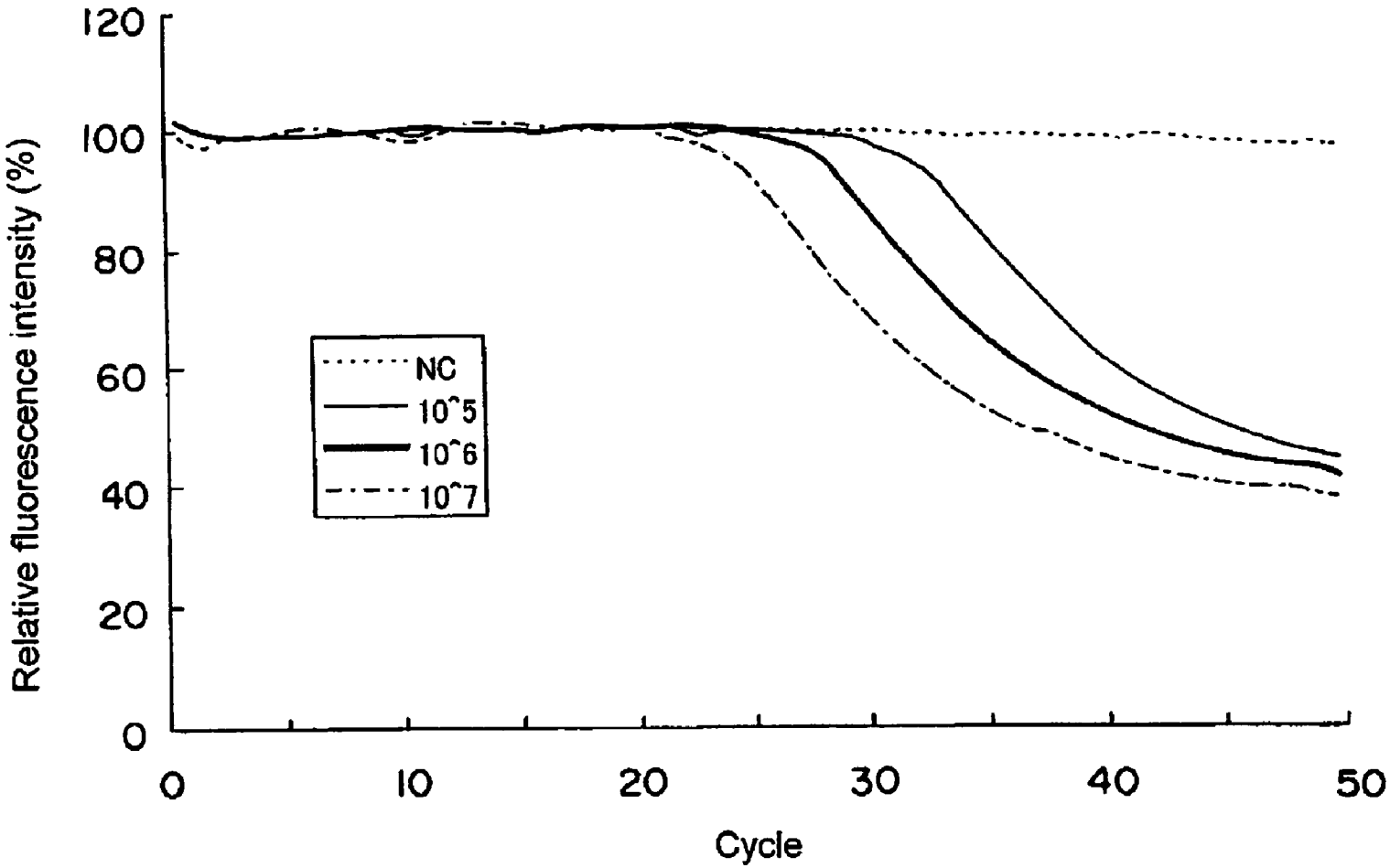
FIG. 1 shows quantification results for the the total sequences obtained by the method of Example 1 (using primers F-24 and R-19).

<1> First Detection Method of the Present Invention

The first detection method of the present invention is a method for detecting a DNA having the mitochondrial DNA 3243 mutation, comprising performing PCR using a DNA obtained from a sample as a template and detecting an amplification product, characterized in that primers used for PCR comprises a primer having a nucleotide sequence complementary to a nucleotide sequence starting from the nucleotide number 243 in the nucleotide sequence of SEQ ID NO: 2 and having a length of 12 to 30 nucleotides.

The sample is not particularly limited so long as it contains mitochondria. Examples thereof include blood, oral swab, tissue and so forth. DNAs can be obtained from these samples in an ordinary manner under conditions under which mitochondrial DNAs can be prepared.

PCR in the first detection method of the present invention can be performed by a usual PCR method except that a DNA obtained from a sample is used as a template, and specific primers are used.

The primers used in the present invention comprise a primer having a nucleotide sequence complementary to a nucleotide sequence starting from the nucleotide number 243 in the nucleotide sequence of SEQ ID NO: 2 and having a length of 12 to 30 nucleotides. That is, one of the primers used in PCR is a primer having a nucleotide sequence complementary to a nucleotide sequence starting from the nucleotide number 243 in the nucleotide sequence of SEQ ID NO: 2 and having a length of 12 to 30 nucleotides.

The 3' end of this primer is the site of the mt3243 mutation. Accordingly, an extension reaction by a DNA polymerase occurs only when this primer anneals, and thus a DNA having the mutant type sequence is specifically amplified. Therefore, a DNA having the mt3243 mutation can be detected by detecting the amplification product.

The primers used for PCR can be designed in the same manner as in a method for designing a primer pair for usual PCR except that they are designed in a region enabling PCR and comprise a primer designed so that the 3' end thereof should be the mt3243 mutation site as described above. The length and Tm of the primers are usually 12- to 40-mer and 40 to 70° C., preferably 16- to 30-mer and 55 to 60° C., respectively. Primers of the primer pair may not be equal in length. However, it is preferred that the Tm values of the primers are substantially equal (the difference is usually within 2° C.). The Tm values are values calculated by the nearest neighbor method. Examples of the primer pair include primers having the nucleotide sequences of SEQ ID NOS: 3 and 5.

The aforementioned primer pair in a specific region can be designed according to a method known to those skilled in the art taking PCR conditions into consideration. The primer pair can be designed by using a computer program for designing primers.

PCR conditions can be selected according to a usual PCR method. A typical example of the composition of the PCR reaction mixture used for the first detection method of the present invention is as follows.

TABLE 1

| | |
|---|---|
| DNA fragments | $10^1$ to $10^8$ molecules/reaction |
| Primers | 200 to 1000 nM |
| Nucleotides | 20 to 200 μM each |
| DNA polymerase | 0.01 to 0.03 U/μl |
| Tris-HCl (pH 8.4 to 9.0) | 5 to 20 mM |
| $MgCl_2$ | 1.5 to 3 mM |
| KCl | 10 to 100 mM |
| Glycerol | 0 to 20% |
| (Final liquid volume: 10 to 100 μl) | |

Further, a typical example of the temperature cycle used for the first detection method of the present invention is as follows, and this temperature cycle is usually repeated 25 to 40 times.

(1) Denaturation at 90 to 98° C. for 1 to 60 seconds
(2) Annealing at 60 to 70° C. for 10 to 60 seconds
(3) Extension at 60 to 75° C. for 10 to 180 seconds When annealing and extension are performed in one step, conditions of 60 to 70° C. for 10 to 180 seconds may be used, for example.

In the first detection method of the present invention, an amplification product can be detected according to a usual method for detecting an amplification product. For example, the amplification product may be detected by agarose gel electrophoresis, or measuring fluorescence in the presence of a substance of which fluorescence changes when it binds to the amplification product (for example, a fluorescent dye that binds to a double-stranded DNA, of which fluorescence intensity changes due to the binding etc.).

<2> Quantification Method of the Present Invention

The quantification method of the present invention is a method for quantifying a DNA having the mitochondrial DNA 3243 mutation, comprising performing quantitative PCR using a DNA obtained from a sample as a template and quantifying an amplification product, and characterized in that the quantitative PCR is a method of using a system in which fluorescence changes depending on amount of an amplification product to quantify the amplification product in PCR on real time basis by measurement of fluorescence and quantifying the DNA in the sample on the basis of the result of the measurement, and primers used for quantitative PCR comprise a primer having a nucleotide sequence complementary to a nucleotide sequence starting from the nucleotide number 243 in the nucleotide sequence of SEQ ID NO: 2 and having a length of 12 to 30 nucleotides.

Preparation of DNA from the sample and primers are as explained above with regard to the detection method of the present invention.

The quantitative PCR, in which the amplification product of PCR is quantified on real time basis by using a system in which fluorescence changes depending on the amount of amplification product and measuring the fluorescence, and a DNA in the sample is quantified on the basis of the result, can be performed according to a known method. Examples of such a method include a method of using a fluorescence-labeled probe that hybridizes with the amplification product, a method of using a reagent that specifically binds to double-stranded DNA and so forth.

Examples of the fluorescence-labeled probe include a probe bound with a fluorescent dye at the 5' end and bound with a quenching substance that absorbs energy emitted from the fluorescent dye at the 3' end (for example, TaqMan® Probe), a nucleic acid probe of which end is labeled with a fluorescent dye of which fluorescence decreases upon hybridization (for example, see Japanese Patent Application Laid-open No. 2002-119291) and so forth.

A probe that can be used in the present invention will be explained below by referring, as an example, to a nucleic acid probe of which end is labeled with a fluorescent dye of which fluorescence decreases upon hybridization (quenching probe). In this embodiment, the quenching probe is designed so that, when the probe hybridizes with a target nucleic acid, the probe-nucleic acid hybrid comprising two or more nucleotide pairs should form at least one pair of G and C in the end portion. Examples of the probe designed as described above and having a 5' end labeled with a fluorescent dye include those having a nucleotide sequence starting from the nucleotide number 212 or 215 in the nucleotide sequence of SEQ ID NO: 1 and having a length of 15 to 40 nucleotides or a nucleotide sequence starting from the nucleotide number 222 in the nucleotide sequence of SEQ ID NO: 2 and having a length of 15 to 40 nucleotides. Further, examples of the probe having a 3' end labeled with a fluorescent dye include those having a nucleotide sequence complementary to a nucleotide sequence starting from the nucleotide number 230 in the nucleotide sequence of SEQ ID NO: 2 and having a length of 14 to 40 nucleotides.

The quenching probe used in the present invention may be the same as the quenching probe described in Japanese Patent Application Laid-open No. 2002-119291 except that it should have such a nucleotide sequences as described above. Examples of the nucleotide sequence of the quenching probe used in the present invention include the sequences of SEQ ID NOS: 6 to 10. As the fluorescent dye, those described in Japanese Patent Application Laid-open No. 2002-119291 can be used, and specific examples thereof include FAM (trademark), TAMRA (trademark), BODIPY (trademark) FL and so forth. The fluorescent dye can be bound to an oligonucleotide according to a usual method, for example, by the method described in Japanese Patent Application Laid-open No. 2002-119291.

The quantification method of the present invention can be performed according to a real time PCR method based on measurement of fluorescence of a fluorescent dye except that a region containing the mt3243 mutation in a mitochondrial DNA is amplified by using a specific primer pair. In the quantification method of the present invention, amplification is performed in the presence of the aforementioned probe, and the amplification reaction conditions and so forth can be easily adjusted by those skilled in the art depending on the used probe.

A typical example of the composition of the PCR reaction mixture used for the quantification method of the present invention is as follows.

TABLE 2

| | |
|---|---|
| DNA fragments | $10^1$ to $10^8$ molecules/reaction |
| Primers | 200 to 1000 nM |
| Probe | 100 to 1000 nM |
| Nucleotides | 20 to 200 μM each |
| DNA polymerase | 0.01 to 0.03 U/μl |
| Tris-HCl (pH 8.4 to 9.0) | 5 to 20 mM |
| $MgCl_2$ | 1.5 to 3 mM |
| KCl | 10 to 100 mM |
| Glycerol | 0 to 20% |
| (Final liquid volume: 10 to 100 μl) | |

Further, a typical example of the temperature cycle is as follows, and this temperature cycle is usually repeated 25 to 40 times.

(1) Denaturation at 90 to 98° C. for 1 to 60 seconds
(2) Annealing at 60 to 70° C. for 10 to 60 seconds
(3) Extension at 60 to 75° C. for 10 to 180 seconds When annealing and extension are performed in one step, conditions of 60 to 70° C. for 10 to 180 seconds can be mentioned, for example.

In the quantification method of the present invention, the detection is performed while PCR is being performed. Therefore, it is not necessary to handle the amplification product after completion of the reaction. Accordingly, there is no risk of contamination with the amplification product. Further, the detection is performed while PCR is being performed, time required for the detection can be markedly reduced. Furthermore, because the detection is performed with the same equipment as required for the amplification, it is not necessary to move a vessel. Therefore, automatization of the method is also easy. Further, because restriction enzymes are not used, the method shows superior quantitativity.

This method is also highly sensitive and enables detection even for a heteroplasmy ratio of 1% or lower. Therefore, by quantifying a DNA having the mt3243 mutation by the aforementioned quantification method and quantifying the total mitochondrial DNAs, the heteroplasmy ratio of mt3243 mutation can be obtained on the basis of the results of those quantifications. That is, the present invention provides a method for determining the heteroplasmy ratio of mt3243 mutation. The determination method of the present invention is characterized by comprising (a) quantifying a DNA having the mitochondrial DNA 3243 mutation by the quantification method of the present invention, (b) quantifying mitochondrial DNAs by a method for quantifying mitochondrial DNAs comprising performing quantitative PCR using a DNA obtained from a sample as a template and quantifying an amplification product, wherein the quantitative PCR uses a system in which fluorescence changes depending on amount of an amplification product to quantify the amplification product of PCR on real time basis by measurement of fluorescence, and the DNAs in the sample are quantified on the basis of the result of the measurement, and (c) calculating the heteroplasmy ratio of the mitochondrial DNA 3243 mutation from the results of (a) and (b).

The step (b) can be performed in the same manner as in the step (a) except that the primers are designed so that mitochondrial DNAS can be amplified regardless of the presence or absence of the mt3243 mutation.

The primer pair used for PCR in the step (b) can be designed in the same manner as in a method for designing a primer pair for usual PCR. The length and Tm of the primers are usually 12- to 40-mer and 40 to 70° C., preferably 16- to 30-mer and 55 to 60° C., respectively. Primers of the primer pair may not be equal in length. However, it is preferred that the Tm values of the primers are substantially equal (the difference is usually within 2° C.). The Tm values are values calculated by the nearest neighbor method. The primer pair used in the step (b) preferably overlaps the primer pair used in the step (a) in most parts. By designing the primer pairs as described above, influence of the differences between the primer pairs on amplification efficiency can be reduced, and a correct heteroplasmy ratio can be obtained. Examples of the primer pair include a pair of primers having the nucleotide sequences of SEQ ID NOS: 3 and 4.

Because a quantified value for the mutant type mitochondrial DNAs can be obtained in the step (a), and a quantified value for the total mitochondrial DNAs can be obtained in the step (b), the heteroplasmy ratio can be obtained by dividing the quantified value of (a) with the quantified value of (b). Because the quantification results of the steps (a) and (b) are used in the step (c), the steps (a) and (b) may be simultaneously performed, or either one of them may be performed first.

<3> Detection Kit of the Present Invention

The detection kit of the present invention is a kit used for the first detection method of the present invention. This kit is characterized by including a primer having a nucleotide sequence complementary to a nucleotide sequence starting from the nucleotide number 243 in the nucleotide sequence of SEQ ID NO: 2 and having a length of 12 to 30 nucleotides.

The primers are as explained in the above with regard to the detection method of the present invention.

In the detection kit of the present invention, primers may be supplied as a mixture or separately included.

The detection kit of the present invention may further include reagents required for PCR and/or the detection of amplification product in addition to the primers.

<4> Quantification Kit of the Present Invention

The quantification kit of the present invention is a kit used for the quantification method of the present invention. This kit is characterized by including a primer having a nucleotide sequence complementary to a nucleotide sequence starting from the nucleotide number 243 in the nucleotide sequence of SEQ ID NO: 2 and having a length of 12 to 30 nucleotides.

The quantification kit of the present invention preferably includes a nucleic acid probe (quenching probe) of which 5' end is labeled with a fluorescent dye, and in which fluorescence of the fluorescent dye decreases upon hybridization, wherein the nucleic acid probe has a nucleotide sequence starting from the nucleotide number 212 or 215 in the nucleotide sequence of SEQ ID NO: 1 and having a length of 15 to 40 nucleotides or a nucleotide sequence starting from the nucleotide number 222 in the nucleotide sequence of SEQ ID NO: 2 and having a length of 15 to 40 nucleotides.

The primers and the quenching probe are as explained above with regard to the quantification method of the present invention.

The quantification kit of the present invention may further include reagents required for PCR in the quantification method of the present invention in addition to the quenching probe. When the quantification kit of the present invention is used to measure the heteroplasmy ratio, the primer pair in the quantification kit of the present invention used in the step (b) preferably overlaps the primer pair used in the step (a) in most parts.

In the quantification kit of the present invention, the quenching probe, primers and other reagents may be separately included, or a part thereof may be provided as a mixture.

<5> Probe of the Present Invention and Second Detection Method of the Present Invention The probe of the present invention is a nucleic acid probe of which end is labeled with a fluorescent dye, and in which fluorescence of the fluorescent dye decreases upon hybridization, wherein the probe has a nucleotide sequence complementary to a nucleotide sequence starting from the nucleotide number 230 in the nucleotide sequence of SEQ ID NO: 2 and having a length of 14 to 40 nucleotides, and the 3' end of the probe is labeled with the fluorescent dye.

The probe of the present invention may be similar to the quenching probe described in Japanese Patent Application Laid-open No. 2002-119291 except that it has a nucleotide sequence complementary to a nucleotide sequence starting from the nucleotide number 230 in the nucleotide sequence of SEQ ID NO: 2 (sequence having the mutant type nucleotide in the mt3243 mutation) and having a length of 14 to 40 nucleotides. Examples of the nucleotide sequence of the quenching probe used in the present invention include the nucleotide sequences of SEQ ID NOS: 21 and 22. As the fluorescent dye, those described in Japanese Patent Application Laid-open No. 2002-119291 can be used, and specific examples thereof include FAM (trademark), TAMRA (trademark), BODIPY (trademark) FL and so forth. The fluorescent dye can be bound to an oligonucleotide in an ordinary manner, for example, by the method described in Japanese Patent Application Laid-open No. 2002-119291.

The second detection method of the present invention is a method for detecting a mutation by performing a melting curve analysis for a nucleic acid having a single nucleotide polymorphism site by using a nucleic acid probe labeled with a fluorescent dye and measuring fluorescence of the fluorescent dye, and detecting the mutation on the basis of the result of the melting curve analysis, and characterized in that the single nucleotide polymorphism is the 3243 mutation, and the nucleic acid probe is the probe of the present invention.

The second detection method of the present invention can be performed according to usual methods for nucleic acid amplification and melting curve analysis (Tm analysis) except that a region containing the mt3243 mutation is amplified, and the probe of the present invention is used.

As the method for nucleic acid amplification, a method of using a polymerase is preferred, and examples thereof include PCR, ICAN, LAMP and so forth. When -amplification is performed by a method using a polymerase, amplification is preferably performed in the presence of the probe of the present invention. The reaction conditions of the amplification and others can be easily adjusted depending on the used probe by those skilled in the art. In this method, only Tm of the probe is analyzed after amplification of a nucleic acid, and therefore it is not necessary to handle the amplification product after completion of the reaction. Thus, there is no risk of contamination with the amplification product. Further, because the detection is performed with the same equipment as required for the amplification, it is not even necessary to move a vessel. Therefore, automatization of the method is also easy.

The method will be further explained below by referring, as an example, to a case of using PCR. The primer pair used for PCR can be designed in the same manner as in a method for designing a primer pair in usual PCR except that it is designed so that a region to which the probe of the present invention is hybridizable should be amplified. The length and Tm of the primers are usually 12- to 40-mer and 40 to 70° C., preferably 16- to 30-mer and 55 to 60° C., respectively. Primers of the primer pair may not be equal in length. However, it is preferred that the Tm values of the primers are substantially equal (the difference is usually within 2° C.). The Tm values are values calculated by the nearest neighbor method. Examples of the primer pair include a primer pair comprising primers having the nucleotide sequences of SEQ ID NOS: 11 and 12.

PCR is preferably performed in the presence of the probe of the present invention. This enables the Tm analysis without performing any operation of handling the amplification product after completion of the amplification reaction. Tm values of primers and reaction conditions of PCR can be easily adjusted by those skilled in the art depending on the used probe.

A typical example of the composition of the reaction mixture for PCR is as follows.

TABLE 3

| | |
|---|---|
| DNA fragments | $10^1$ to $10^8$ molecules/reaction |
| Primers | 200 to 1000 nM |
| Probe | 100 to 1000 nM |
| Nucleotides | 20 to 200 μM each |
| DNA polymerase | 0.01 to 0.03 U/μl |
| Tris-HCl (pH 8.4 to 9.0) | 5 to 20 mM |
| $MgCl_2$ | 1.5 to 3 mM |
| KCl | 10 to 100 mM |
| Glycerol | 0 to 20% |
| (Final fluid volume: 10 to 100 μl) | |

Further, a typical example of the temperature cycle is as follows, and this temperature cycle is usually repeated 25 to 40 times.

(1) Denaturation at 90 to 98° C. for 1 to 60 seconds (2) Annealing at 60 to 70° C. for 10 to 60 seconds (3) Extension at 60 to 75° C. for 10 to 180 seconds When annealing and extension are performed in one step, conditions of 60 to 70° C. for 10 to 180 seconds can be mentioned, for example.

The Tm analysis can be performed in a conventional manner except that fluorescence of the fluorescent dye binding to the probe of the present invention is measured. Fluorescence can be measured by using excitation light having a wavelength suitable for the fluorescent dye and measuring intensity of light of the emission wavelength. The temperature increasing rate in the Tm analysis is usually 0.1 to 1° C. per second. Composition of the reaction mixture for Tm analysis is not particularly limited so long as a probe and a nucleic acid having a sequence complementary to the nucleotide sequence of the prove can hybridize to each other. However, the monovalent cation concentration is usually 1.5 to 5 mM, and pH is usually 7 to 9. Because a reaction mixture for an amplification method using a DNA polymerase such as PCR usually satisfies these conditions, the reaction mixture after the amplification can be used as it is for the Tm analysis.

The mt3243 mutation can be detected on the basis of the results of the Tm analysis in an ordinary manner. The detection in the second detection method of the present invention include not only detection of the presence or absence of a mutation, but also quantification of mutant type DNA and determination of the ratio of wild type DNA and mutant type DNA.

<6> Kit of the Present Invention

The kit of the present invention is a kit used for the second detection method of the present invention. This kit is characterized by including a nucleic acid probe of which end is labeled with a fluorescent dye and in which fluorescence of the fluorescent dye decreases upon hybridization (quenching probe), wherein the probe has a nucleotide sequence complementary to a nucleotide sequence starting from the nucleotide number 230 in the nucleotide sequence of SEQ ID NO: 2 and having a length of 14 to 40 nucleotides, and the 3' end of the probe is labeled with the fluorescent dye.

The quenching probe is as explained above with regard to the probe of the present invention.

The kit of the present invention may include reagents required for amplification of a nucleic acid in the second detection method of the present invention, in particular, primers for amplification using a DNA polymerase, in addition to the quenching probe.

In the kit of the present invention, the quenching probe, primers and other reagents may be separately included, or a part thereof may be provided as a mixture.

EXAMPLES

The present invention will be explained more specifically with reference to the following examples.

Example 1

The primers shown in Table 4 were designed on the basis of the nucleotide sequence containing the site of human mitochondrial 3243 A→G mutation (mt3243 mutation) (SEQ ID NO: 2, the nucleotide number 243 corresponds to the 3243rd position in the mitochondrial gene) so that a region containing the mt3243 mutation could be amplified. In Table 4, the positions are indicated with the nucleotide numbers in the nucleotide sequence of SEQ ID NO: 2.

TABLE 4

| Primers Name | Sequence (5' → 3') | mer | Position | SEQ ID NO: |
|---|---|---|---|---|
| F-24 | ctcaacttagtattatacccacac | 24 | 187-210 | 3 |
| R-19 | ttttatgcgattaccgggc | 19 | 262-244 | 4 |
| R-mt-16 | atgcgattaccgggcc | 16 | 258-243 | 5 |

Then, probes having C at the ends shown in Table 5 were designed. In Table 5, the positions are indicated with the nucleotide numbers in the nucleotide sequence of SEQ ID NO: 1 or 2. Further, the capital letters in the nucleotide sequences represent sites of the mt3243 mutation, and (P) at the 3' ends means being phosphorylated. The probe was labeled with BODIPY (trademark) FL in a conventional manner.

TABLE 5

| Probes Name | Sequence (5' → 3') | mer | Position |
|---|---|---|---|
| 5FL-mut-5-23 | (BODIPY FL)-cagggtttgttaagatggcagGg-(P) (SEQ ID NO: 6) | 23 | 222-244 |
| 5FL-1-24 | (BODIPY FL)-ccaagaacagggtttgttaagatg-(P) (SEQ ID NO: 7) | 24 | 215-238 |
| 5FL-1-26 | (BODIPY FL)-ccaagaacagggtttgttaagatggc-(P) (SEQ ID NO: 8) | 26 | 215-240 |
| 5FL-1-28 | (BODIPY FL)-ccaagaacagggtttgttaagatggcag-(P) (SEQ ID NO: 9) | 28 | 215-242 |
| 5FL-3-30 | (BODIPY FL)-cacccaagaacagggtttgttaagatggca-(P) (SEQ ID NO: 10) | 30 | 212-241 |

Real time PCR was performed by using a plasmid incorporated with a region around the mt3243 mutation as a sample and iCycler (Bio-Rad) under the conditions shown below. The excitation wavelength and detection wavelength in the real time analysis were 490 nm and 530 nm, respectively.

TABLE 6

| Compositions of Reaction mixture | |
|---|---|
| 1. System for quantification of both normal sequence and mutant type sequence (system for quantification of total mitochondrial DNA number) | |
| $H_2O$ | 17.575 μL |
| 10 × Gene Taq buffer | 2.5 μL |
| 40% Glycerol | 1.875 μL |
| 10 mM each dATP, dUTP, dGTP, dCTP | 0.5 μL |
| 2 U/μL Uracil-N-glycosylase | 0.05 μL |
| 5 μM Probe | 1 μL |
| 100 μM Primer F-24 | 0.125 μL |
| 100 μM Primer R-19 | 0.25 μL |
| 5 U/μL Gene Taq | 0.125 μL |
| Sample | 1 μL |
| Total | 25 μL |
| 2. System for quantification of mutant type sequence (system for quantification of number of mitochondrial DNAs having mutation) | |
| $H_2O$ | 18.825 μL |
| 10 × Gene Taq buffer | 2.5 μL |
| 40% Glycerol | 0.625 μL |
| 10 mM each dATP, dUTP, dGTP, dCTP | 0.5 μL |
| 2 U/μL Uracil-N-glycosylase | 0.05 μL |
| 5 μM Probe | 1 μL |

TABLE 6-continued

| Compositions of Reaction mixture | |
|---|---|
| 100 μM Primer F-24 | 0.125 μL |
| 100 μM Primer R-mt-16 | 0.25 μL |
| 5 U/μL Gene Taq | 0.125 μL |
| Sample | 1 μL |
| Total | 25 μL |

TABLE 7

| Reaction conditions | |
|---|---|
| 50° C., 2 min | |
| ↓ | |
| 95° C., 2 min | |

TABLE 7-continued

| Reaction conditions | |
|---|---|
| ↓ | |
| 95° C., 10 sec | |
| 56° C., 30 sec | (50 cycles) |

Samples containing plasmids having the normal type sequence in various copy numbers were prepared as samples, and quantification was performed by using the probe 5FL-3-30 as the probe in the system 1 mentioned above. The results are shown in FIG. 1. As seen from the results shown in the drawing, it was confirmed that quantification was possible.

Figure 2:
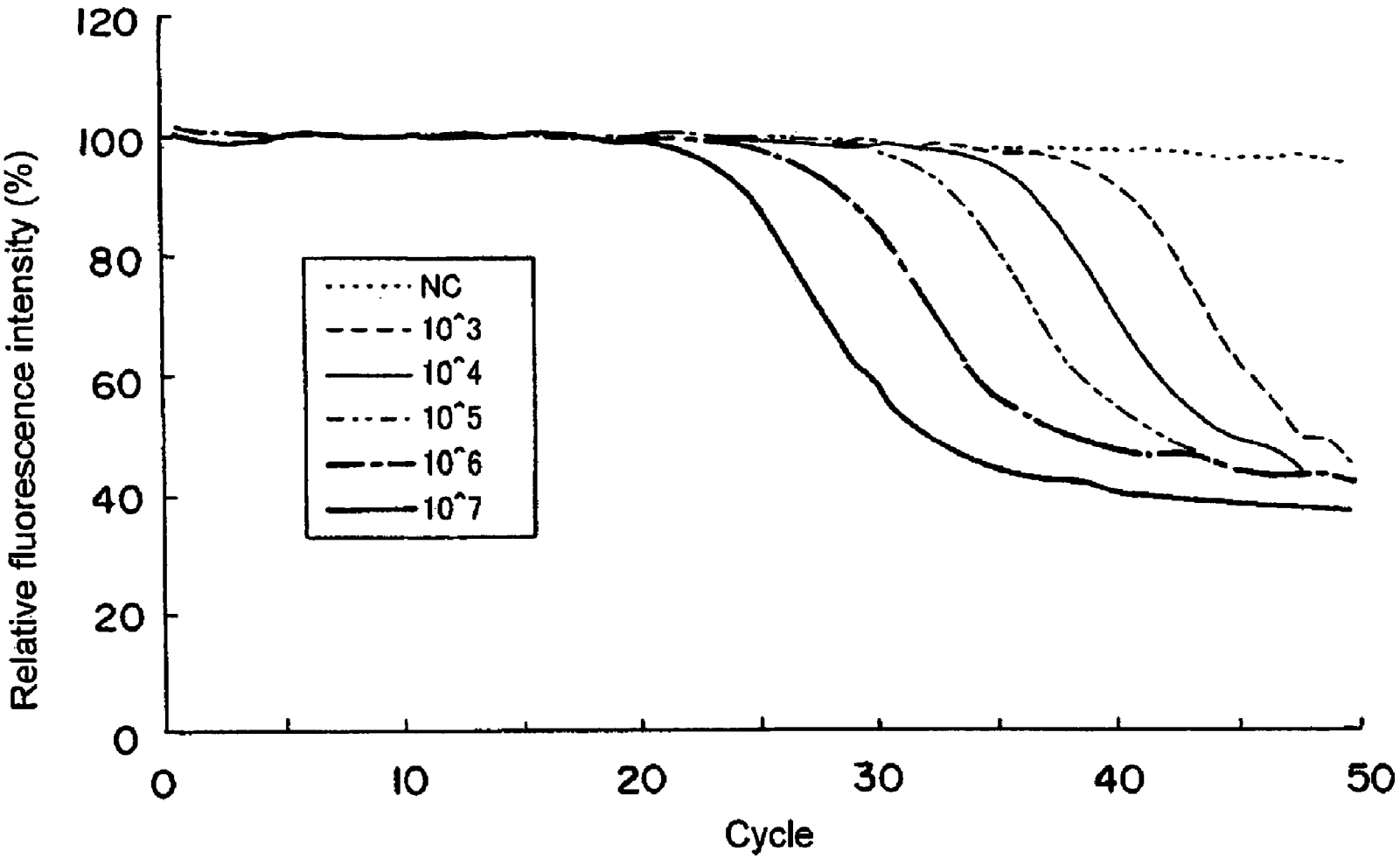
FIG. 2 shows quantification results for the mutant type sequences obtained by the method of Example 1 (using primers F-24 and R-mt-16).

Samples containing plasmids having the mutant type sequence in various copy numbers were prepared as samples, and quantification was performed by using the probe 5FL-3-30 as the probe in the system 2 mentioned above. The results are shown in FIG. 2. As seen from the results shown in the drawing, it was confirmed that quantification was possible.

Figure 3:
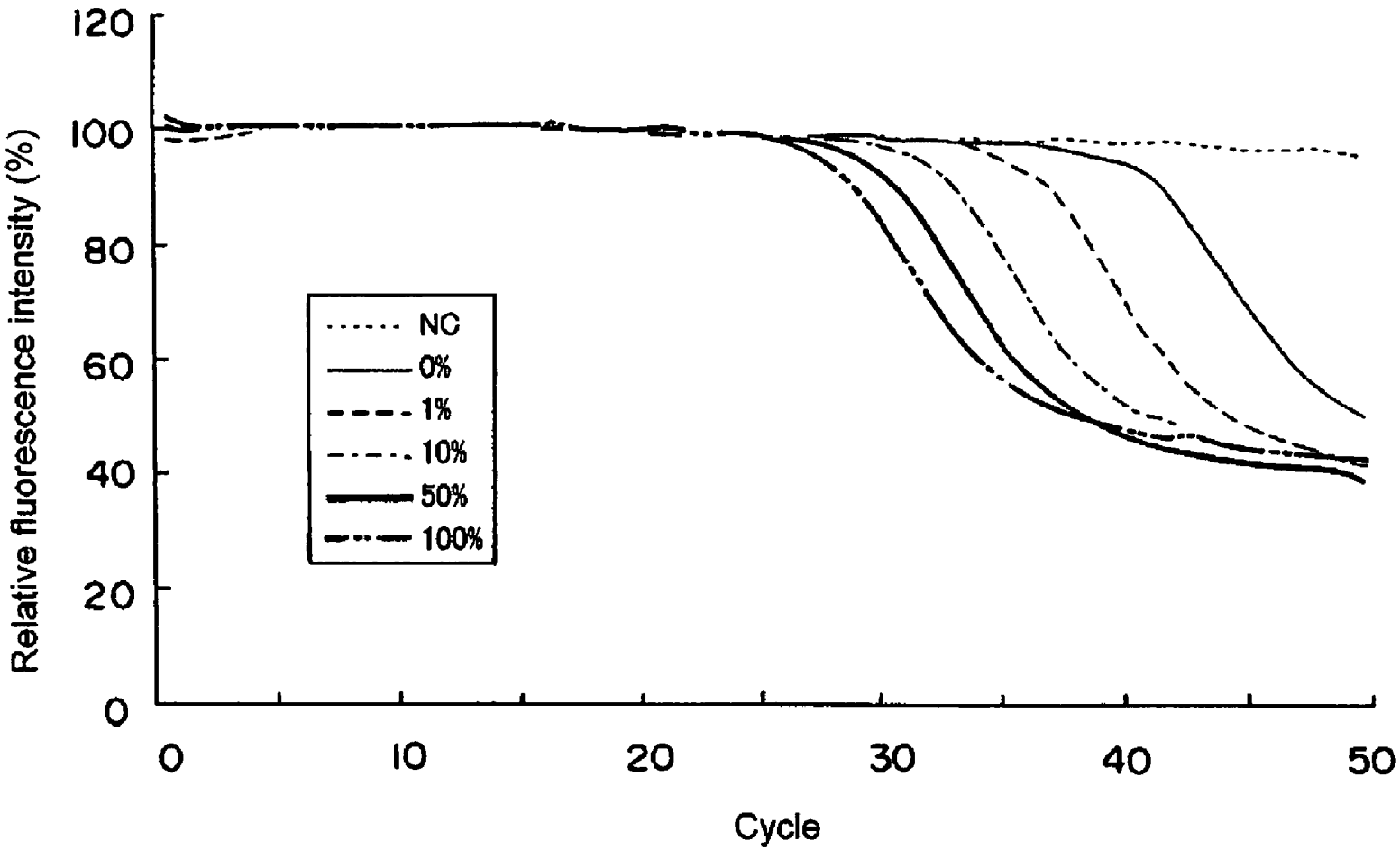
FIG. 3 shows quantification results for samples containing mutant genes in different proportions obtained by the method of Example 1 (using primers F-24 and R-mt-16).

Mixtures of samples containing plasmids having the mutant type sequence and plasmids having the normal type sequence at various ratios were prepared as samples, and quantification was performed by using the probe 5FL-3-30 as the probe in the system 2 mentioned above. The results are shown in FIG. 3. When the same samples were quantified by using the system 1 mentioned above, and the ratio of the mutant type sequence was calculated, results consistent with the ratios at the time of preparation of the samples were obtained.

When probes 5FL-1-24, 5FL-1-26, 5FL-1-28 and 5FL-mut-5-23 were used as the probes, similar results were also obtained.

In FIGS. 1 to 3, the vertical axis represents fluorescence intensity relative to the intensity at the start of the reaction, which was taken as 100%, and the horizontal axis represents the number of PCR cycles.

Example 2

The primers shown in Table 8 were designed on the basis of the nucleotide sequence containing the site of human mitochondria 3243 A→G mutation (mt3243 mutation) (SEQ ID NO: 2, the nucleotide number 243 corresponds to the 3243rd position in the mitochondrial gene) so that a region containing the mt3243 mutation could be amplified. In Table 8, the positions are indicated with the nucleotide numbers in the nucleotide sequence of SEQ ID NO: 1.

TABLE 8

| Primers Name | Sequence (5' → 3') | mer | Position | SEQ ID NO: |
|---|---|---|---|---|
| F-27 | catctcaacttagtattatacccacac | 27 | 184-210 | 11 |
| R-22 | agaggaattgaacctctgactg | 22 | 296-275 | 12 |

Then, the probes having C at the ends shown in Table 9 were designed. In Table 9, the positions are indicated with the nucleotide numbers in the nucleotide sequence of SEQ ID NO: 1. Further, the capital letters in the nucleotide sequences represent sites of the mt3243 mutation, and (P) at the 3' ends means being phosphorylated. The probes were labeled with BODIPY (trademark) FL or TAMRA (trademark) in a conventional manner.

TABLE 9

| Probes Name | Sequence (5' → 3') | Mer | Position | SEQ ID NO: |
|---|---|---|---|---|
| 3FL-mt-F3-20 | tttgttaagatggcagGgcc-(BODIPY FL) | 20 | 227-246 | 13 |
| 3T-mt-F2-21 | tttgttaagatggcagGgccc-(TAMRA) | 21 | 227-247 | 14 |
| 3T-mt-R1-22 | gcgattaccgggcCctgccatc-(TAMRA) | 22 | 256-235 | 15 |
| 5T-mt-R2-20 | (TAMRA)-ccgggcCctgccatcttaac-(P) | 20 | 249-230 | 16 |
| 3T-mt-F2-17 | ttaagatggcagGgccc-(TAMRA) | 17 | 231-247 | 17 |
| 3T-mt-F3-16 | ttaagatggcagGgcc-(TAMRA) | 16 | 231-246 | 18 |
| 3T-mt-R1-20 | gattaccgggcCctgccatc-(TAMRA) | 20 | 254-235 | 19 |
| 3T-mt-F1-16 | gcagGgcccggtaatc-(TAMRA) | 16 | 239-254 | 20 |
| 3T-mt-R2-18 | gggcCctgccatcttaac-(TAMRA) | 18 | 247-230 | 21 |
| 3T-mt-R2-17 | ggcCctgccatcttaac-(TAMRA) | 17 | 246-230 | 22 |
| 3FL-mt-R2-18 | gggcCctgccatcttaac-(BODIPY FL) | 18 | 247-230 | 21 |
| 3FL-mt-R2-17 | ggcCctgccatcttaac-(BODIPY FL) | 17 | 246-230 | 22 |

PCR and Tm analysis were performed by using a plasmid incorporated with a region around the mt3243 mutation as a sample and Smart Cycler System (Cephied) under the conditions shown below. The excitation wavelength and the detection wavelength in the Tm analysis were 450 to 495 nm and 505 to 537 nm (BODIPY FL) and 527 to 555 nm and 565 to 605 nm (TAMRA), respectively.

TABLE 10

| Composition of reaction mixture | |
|---|---|
| $H_2O$ | 15.995 μL |
| 10 × Gene Taq buffer | 2.5 μL |
| 40% Glycerol | 3.125 μL |
| 10 mM each dATP, dUTP, dGTP, dCTP | 0.5 μL |
| 2 U/μL Uracil-N-glycosylase | 0.05 μL |
| 5 μM Probe | 1 μL |
| 100 mM $MgCl_2$ | 0.375 μL |
| 100 μM Primer F-27 | 0.25 μL |
| 100 μM Primer R-22 | 0.125 μL |
| 5 U/μL Gene Taq FP | 0.125 μL |
| Sample (0 to 2000 copies) | 1 μL |
| Total | 25 μL |

TABLE 11

| Reaction conditions | |
|---|---|
| 50° C., 2 min<br>↓<br>95° C., 2 min<br>↓<br>95° C., 1 sec<br>66° C., 18 sec<br>↓<br>Tm analysis (1° C./sec) | (50 cycles) |

Figure 4:
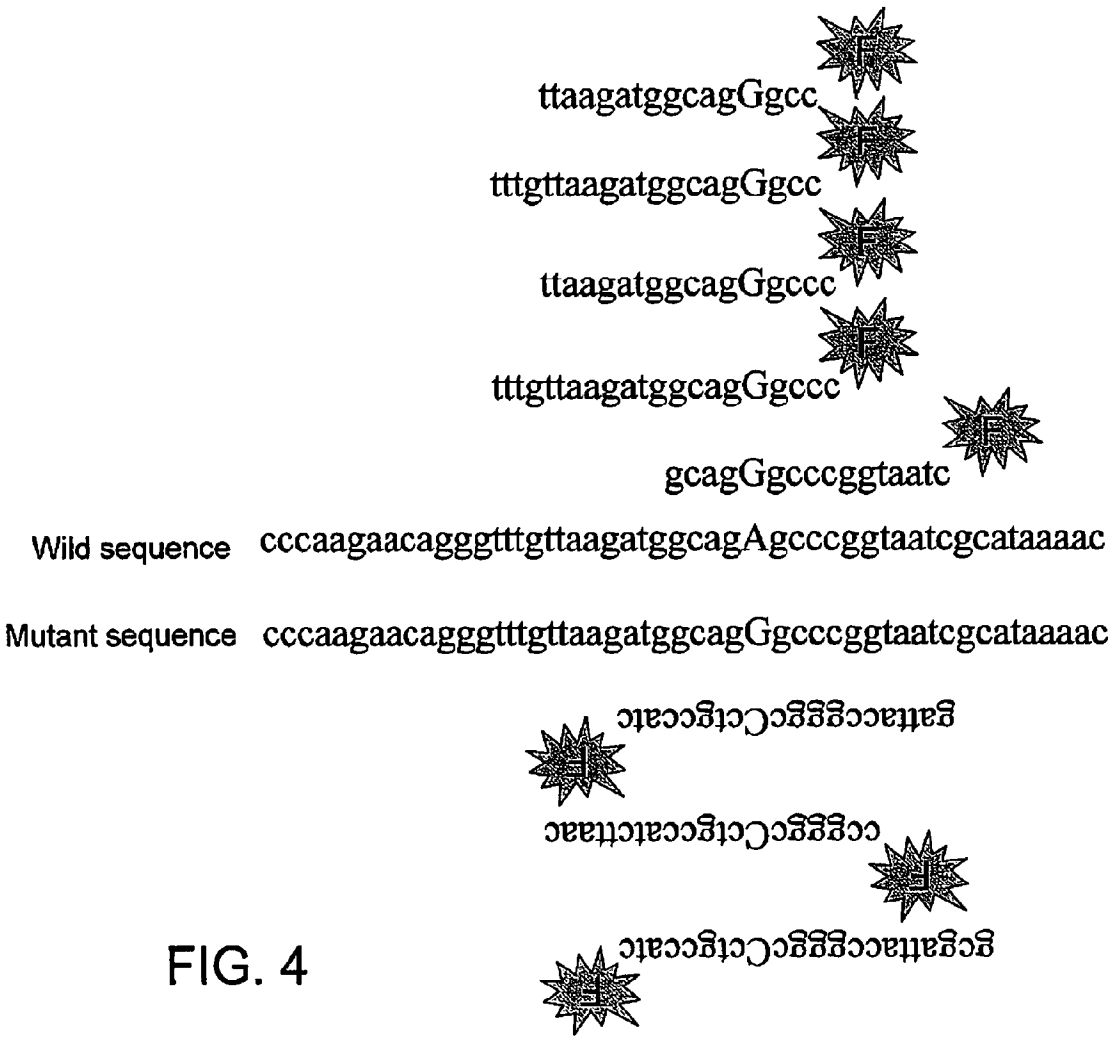
FIG. 4 shows positions of quenching probes that cannot identify a mutation. The sequences shown correspond to the following SEQ ID NOS from top to bottom: SEQ ID NO: 18, SEQ ID NO: 13, SEQ ID NO: 17, SEQ ID NO: 14, SEQ ID NO: 20, Wild sequence (positions 214-263 of SEQ ID NO: 1), Mutant sequence (positions 214-263 of SEQ ID NO: 2), SEQ ID NO: 19, SEQ ID NO: 16, and SEQ ID NO: 15.
Figure 5:
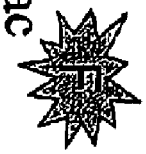
FIG. 5 shows positions of quenching probes that can identify a mutation. The sequences shown correspond to the following SEQ ID NOS from top to bottom: Wild sequence (positions 214-263 of SEQ ID NO: 1), Mutant sequence (positions 214-263 of SEQ ID NO: 2), SEQ ID NO: 21 and SEQ ID NO: 20.
Figure 5:
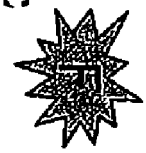

PCR and Tm analysis were performed by using each probe. As a result, only when the probes 3T-mt-R2-18, 3T-mt-R2-17, 3FL-mt-R2-18 and 3FL-mt-R2-17 were used, changes in fluorescence intensity that could be analyzed in Tm analysis were observed. The positions of the probes relative to the nucleotide sequence containing the mt3243 mutation are shown in FIGS. 4 and 5. The wild type sequence and mutant type sequence shown in the drawings correspond to the nucleotide numbers 214 to 263 in the nucleotide sequence of SEQ ID NOS: 1 and 2, respectively. Further, in the drawings, F denotes a fluorescent dye. On the basis of the positions shown in FIGS. 4 and 5, it is considered that whether the probe can be used for Tm analysis depends on the position of C bound with a fluorescent dye, and the length of the probe is not so important so long as the polymorphism site is included.

Figure 6:
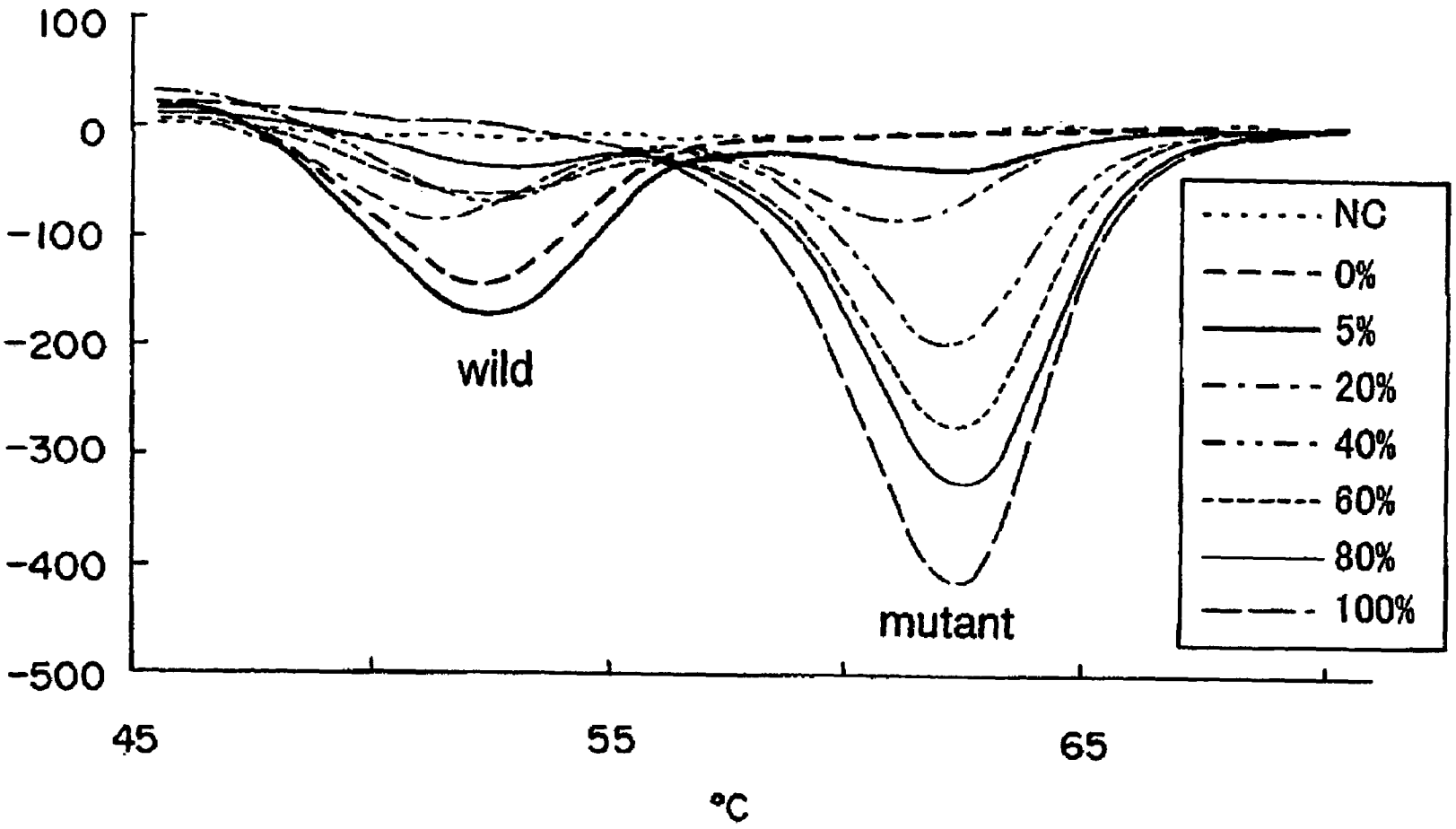
FIG. 6 shows quantification results for samples containing mutant genes in different proportions obtained by the method of Example 2. In the drawing, the "wild" denotes wild type, and "mutant" denotes mutant type.

Mixtures of samples containing plasmids having the mutant type sequence and containing plasmids having the normal type sequence at various ratios were prepared as samples, and quantification was performed by using the probe 3FL-mt-R2-17. The results are shown in FIG. 6. Regardless of the ratio of the mutant type sequence, the mutant type sequence (mutant) and the normal type sequence (wild) could be distinctively detected.

When the probes 3T-mt-R2-18, 3T-mt-R2-17 and 3FL-mt-R2-18 were used, similar results were also obtained.

In FIG. 6, the vertical axis represents a primary derivative value of fluorescence intensity with an inverted sign (−dF/dt), and the horizontal axis represents temperature (° C.).

INDUSTRIAL APPLICABILITY

According to the present invention, methods for detecting and quantifying the mitochondrial DNA 3243 mutation and a kit therefor are provided.

Further, according to the present invention, a quenching probe effective for detecting the mt3243 mutation is provided, and a method for detecting the mt3243 mutation by using it and a kit therefor are further provided. Because the Tm analysis is completed within several tens of seconds, time required for the detection can be markedly reduced. According to a preferred embodiment of the present invention, wherein amplification of nucleic acid in the presence of the probe and Tm analysis are combined, only the Tm of the probe is analyzed after the amplification of nucleic acid, and therefore it is not necessary to handle the amplification product after completion of the reaction. Accordingly, there is no risk of contamination with the amplification product. Further, because the detection can be performed with the same equipment as required for the amplification, it is even unnecessary to move a vessel. Therefore, automatization of the method is also easy.

SEQUENCE LISTING

```
<160> NUMBER OF SEQ ID NOS: 22

<210> SEQ ID NO 1
<211> LENGTH: 500
<212> TYPE: DNA
<213> ORGANISM: Homo sapiens
<220> FEATURE:
<221> NAME/KEY: allele
<222> LOCATION: 243

<400> SEQUENCE: 1

ggacatcccg atggtgcagc cgctattaaa ggttcgtttg ttcaacgatt aaagtcctac     60

gtgatctgag ttcagaccgg agtaatccag gtcggtttct atctaccttc aaattcctcc    120

ctgtacgaaa ggacaagaga aataaggcct acttcacaaa gcgccttccc ccgtaaatga    180

tatcatctca acttagtatt atacccacac ccacccaaga acagggtttg ttaagatggc    240

agagcccggt aatcgcataa aacttaaaac tttacagtca gaggttcaat tcctcttctt    300

aacaacatac ccatggccaa cctcctactc ctcattgtac ccattctaat cgcaatggca    360

ttcctaatgc ttaccgaacg aaaaattcta ggctatatac aactacgcaa aggccccaac    420

gtggtaggcc cctacgggct actacaaccc ttcgctgacg ccataaaact cttcaccaaa    480

gagcccctaa aacccgccac                                                500


<210> SEQ ID NO 2
<211> LENGTH: 500
<212> TYPE: DNA
<213> ORGANISM: Homo sapiens
<220> FEATURE:
<221> NAME/KEY: allele
<222> LOCATION: 243

<400> SEQUENCE: 2

ggacatcccg atggtgcagc cgctattaaa ggttcgtttg ttcaacgatt aaagtcctac     60

gtgatctgag ttcagaccgg agtaatccag gtcggtttct atctaccttc aaattcctcc    120

ctgtacgaaa ggacaagaga aataaggcct acttcacaaa gcgccttccc ccgtaaatga    180

tatcatctca acttagtatt atacccacac ccacccaaga acagggtttg ttaagatggc    240

agggcccggt aatcgcataa aacttaaaac tttacagtca gaggttcaat tcctcttctt    300
```

aacaacatac ccatggccaa cctcctactc ctcattgtac ccattctaat cgcaatggca 360 ttcctaatgc ttaccgaacg aaaaattcta ggctatatac aactacgcaa aggccccaac 420 gtggtaggcc cctacgggct actacaaccc ttcgctgacg ccataaaact cttcaccaaa 480 gagcccctaa aacccgccac 500

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3 ctcaacttag tattataccc acac 24

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4 ttttatgcga ttaccgggc 19

<210> SEQ ID NO 5
<211> LENGTH: 16
<212> TYPE: DNA
<213> ORGANISM: Artificial Sequence
<220> FEATURE:
<223> OTHER INFORMATION: primer

<400> SEQUENCE: 5 atgcgattac cgggcc 16

<210> SEQ ID NO 6
<211> LENGTH: 23
<212> TYPE: DNA
<213> ORGANISM: Artificial Sequence
<220> FEATURE:
<223> OTHER INFORMATION: probe

<400> SEQUENCE: 6 cagggtttgt taagatggca ggg 23

<210> SEQ ID NO 7
<211> LENGTH: 24
<212> TYPE: DNA
<213> ORGANISM: Artificial Sequence
<220> FEATURE:
<223> OTHER INFORMATION: probe

<400> SEQUENCE: 7 ccaagaacag ggtttgttaa gatg 24

<210> SEQ ID NO 8
<211> LENGTH: 26
<212> TYPE: DNA
<213> ORGANISM: Artificial Sequence
<220> FEATURE:
<223> OTHER INFORMATION: probe

<400> SEQUENCE: 8 ccaagaacag ggtttgttaa gatggc 26

<210> SEQ ID NO 9
<211> LENGTH: 28
<212> TYPE: DNA
<213> ORGANISM: Artificial Sequence
<220> FEATURE:
<223> OTHER INFORMATION: probe

<400> SEQUENCE: 9 ccaagaacag ggtttgttaa gatggcag 28

<210> SEQ ID NO 10
<211> LENGTH: 30
<212> TYPE: DNA
<213> ORGANISM: Artificial Sequence
<220> FEATURE:
<223> OTHER INFORMATION: probe

<400> SEQUENCE: 10 cacccaagaa cagggtttgt taagatggca 30

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11 catctcaact tagtattata cccacac 27

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12 agaggaattg aacctctgac tg 22

<210> SEQ ID NO 13
<211> LENGTH: 20
<212> TYPE: DNA
<213> ORGANISM: Artificial Sequence
<220> FEATURE:
<223> OTHER INFORMATION: probe

<400> SEQUENCE: 13 tttgttaaga tggcagggcc 20

<210> SEQ ID NO 14
<211> LENGTH: 21
<212> TYPE: DNA
<213> ORGANISM: Artificial Sequence
<220> FEATURE:
<223> OTHER INFORMATION: probe

<400> SEQUENCE: 14 tttgttaaga tggcagggcc c 21

<210> SEQ ID NO 15
<211> LENGTH: 22
<212> TYPE: DNA
<213> ORGANISM: Artificial Sequence
<220> FEATURE:
<223> OTHER INFORMATION: probe

<400> SEQUENCE: 15 gcgattaccg ggccctgcca tc 22

<210> SEQ ID NO 16
<211> LENGTH: 20
<212> TYPE: DNA
<213> ORGANISM: Artificial Sequence
<220> FEATURE:
<223> OTHER INFORMATION: probe

<400> SEQUENCE: 16 ccgggccctg ccatcttaac 20

<210> SEQ ID NO 17
<211> LENGTH: 17
<212> TYPE: DNA
<213> ORGANISM: Artificial Sequence
<220> FEATURE:
<223> OTHER INFORMATION: probe

<400> SEQUENCE: 17 ttaagatggc agggccc 17

<210> SEQ ID NO 18
<211> LENGTH: 16
<212> TYPE: DNA
<213> ORGANISM: Artificial Sequence
<220> FEATURE:
<223> OTHER INFORMATION: probe

<400> SEQUENCE: 18 ttaagatggc agggcc 16

<210> SEQ ID NO 19
<211> LENGTH: 20
<212> TYPE: DNA
<213> ORGANISM: Artificial Sequence
<220> FEATURE:
<223> OTHER INFORMATION: probe

<400> SEQUENCE: 19 gattaccggg ccctgccatc 20

<210> SEQ ID NO 20
<211> LENGTH: 16
<212> TYPE: DNA
<213> ORGANISM: Artificial Sequence
<220> FEATURE:
<223> OTHER INFORMATION: probe

<400> SEQUENCE: 20 gcagggcccg gtaatc 16

<210> SEQ ID NO 21
<211> LENGTH: 18
<212> TYPE: DNA
<213> ORGANISM: Artificial Sequence
<220> FEATURE:
<223> OTHER INFORMATION: probe

<400> SEQUENCE: 21 gggccctgcc atcttaac 18

<210> SEQ ID NO 22
<211> LENGTH: 17

-continued

```
<212> TYPE: DNA
<213> ORGANISM: Artificial Sequence
<220> FEATURE:
<223> OTHER INFORMATION: probe

<400> SEQUENCE: 22

ggccctgcca tcttaac                                                    17
```

What is claimed is:

[1. A method for detecting a mutation comprising performing a melting curve analysis for a nucleic acid having a single nucleotide polymorphism site by using a nucleic acid probe having a 3' terminal cytosine labeled with a fluorescent dye and measuring fluorescence of the fluorescent dye, and detecting the mutation on the basis of the result of the melting curve analysis, wherein the single nucleotide polymorphism is a mutation at the 3243rd position in a mitochondrial DNA, and the nucleic acid probe consists of the nucleotide sequence of SEQ ID NO: 21 or 22, wherein a region containing the single nucleotide polymorphism site in a nucleic acid contained in a sample is amplified to obtain the nucleic acid showing the single nucleotide polymorphism, and wherein the amplification is performed by a method of using a DNA polymerase in the presence of a nucleic acid probe.]

*2. A method of determining the ratio of a mutant type deoxyribonucleic acid (DNA) of mitochondrial DNA 3243 mutation in a sample comprising:*

*adding to the sample a labeled nucleic acid probe which hybridizes to the mutant type DNA, wherein the probe consists of the nucleotide sequence of SEQ ID NO: 21 or 22,*

*obtaining a melting curve for the probe to the DNA in the sample, and*

*comparing the melting curve for the probe to the DNA in the sample with at least one melting curve with a known mutant ratio, wherein the melting curve with a known mutant ratio indicates the mutant ratio in the sample.*

*3. The method according to claim 2, wherein the probe is labeled with a fluorescent dye, and the melting curve is obtained by detecting fluorescence of the fluorescent dyes.*

*4. The method according to claim 2, wherein the probe consists of the nucleotide sequence of SEQ ID NO: 21.*

*5. The method according to claim 2, wherein the probe consists of the nucleotide sequence of SEQ ID NO: 22.*

*6. The method according to claim 2, further comprising amplifying a region containing the mutation prior to obtaining the melting curve.*

*7. The method according to claim 6, wherein the amplification is performed in the presence of the probe.*

*8. The method according to claim 2, further comprising:*

*adding the probe to a sample with a known mutant ratio,*

*obtaining a melting curve with a known mutant ratio.*

*9. The method according to claim 2, wherein the melting curve for the probe to the DNA in the sample is compared with two or more melting curves with known mutant ratios.*

*10. The method according to claim 2, wherein the probe consists of the nucleotide sequence of SEQ ID NO: 21 or 22 and is labeled with a fluorescent dye, and the melting curve for the probe to the DNA in the sample is compared with two or more melting curves with known mutant ratios.*

*11. A method for detecting a mutation comprising*

*performing a melting curve analysis for a nucleic acid having a single nucleotide polymorphism site by using a nucleic acid probe having a 3' terminal cytosine labeled with a fluorescent dye and*

*measuring fluorescence of the fluorescent dye, and*

*detecting the mutation on the basis of the result of the melting curve analysis, wherein the single nucleotide polymorphism is a mutation at the 3243rd position in a mitochondrial DNA, and the nucleic acid probe consists of the nucleotide sequence of SEQ ID NO: 21 or 22.*

*12. The method according to claim 11,*

*wherein a region containing the single nucleotide polymorphism site in a nucleic acid contained in a sample is amplified to obtain the nucleic acid showing the single nucleotide polymorphism, and*

*wherein the amplification is performed by a method of using a DNA polymerase in the presence of a nucleic acid probe.*

* * * * *